United States Patent [19]

Sicurelli, Jr.

[11] Patent Number: 5,201,656

[45] Date of Patent: Apr. 13, 1993

[54] METHOD AND APPARATUS FOR REPAIRING DENTAL IMPLANTS

[76] Inventor: Robert J. Sicurelli, Jr., 438 Bay Ridge Pkwy., Brooklyn, N.Y. 11209

[21] Appl. No.: 592,718

[22] Filed: Oct. 4, 1990

[51] Int. Cl.$^5$ .................................................. A61C 3/06
[52] U.S. Cl. ........................................ 433/166; 433/173
[58] Field of Search ................... 433/166, 165, 82, 173

[56] References Cited

U.S. PATENT DOCUMENTS

| | | | |
|---|---|---|---|
| 1,499,345 | 7/1924 | Chott | 433/166 |
| 2,707,329 | 5/1955 | Costoff | 433/166 |
| 2,921,373 | 1/1960 | Wiseman | 433/166 |
| 3,478,433 | 11/1969 | Richmond | 433/166 |
| 3,979,829 | 9/1976 | Lemos | 433/165 |
| 4,203,223 | 5/1980 | Lautenschlager et al. | 433/141 |
| 4,364,730 | 12/1982 | Axelsson | 433/141 |
| 4,636,171 | 1/1987 | Martin | 433/166 |
| 4,753,594 | 6/1988 | Croll | 433/166 |
| 4,820,156 | 4/1989 | Ross | 433/173 |

OTHER PUBLICATIONS

The International Journal of Periodontics and Restorative Dentistry, vol. 9, Nov. 4, 1989, p. 303, Prophylactic Modalities.

Primary Examiner—Gene Mancene
Assistant Examiner—Michael Lynch
Attorney, Agent, or Firm—Abdallah & Muckelroy

[57] ABSTRACT

A trephine-type dental drill for polishing the external cylindrical surface of a dental implant in a mouth. The drill includes a shank for mounting upon a dental drill drive, and a mount affixed the shank for mounting an abrasive element. The abrasive element has a hollow circular bore defined by a bore wall which is coated with an abrasive material. The inner bore wall is sized to closely fit and rotationally polish the external cylindrical surface of the dental implant installed within a mouth.

16 Claims, 2 Drawing Sheets

METHOD AND APPARATUS FOR REPAIRING DENTAL IMPLANTS

This invention is directed to a dental implant maintenance and reparative technique and, more particularly, for the removal and polishing off of implant coatings such as titanium, hydroxylapetite, and others, from the surfaces of cylinder, root form, and other types of intra osseous implants that have become exposed and no longer covered by the bone.

These implants are placed in human jaw bones such that the implant is completely covered by the bone.

At times, due to inadequacy of bone or bone resorption, some of the implant protrudes from the bone. This can be caused by lack of bone mass, periodontal disease or peri-implant disease. Because the implant surfaces are rough, they will irritate the periodontal tissues (gums) and retain plaque (food and bacterial residual products). This will cause further inflammation of the peri-implant tissues (gum and bone), and ultimately result in further bone resorption and more of the implant being exposed from the bone. Over time, the implant will fail.

To arrest this vicious cycle, it becomes necessary to remove the exposed implant coating and polish the undersurface to achieve a smooth finish. This surface can remain more plaque free and therefore more maintainable.

One technique which has been shown to be somewhat effective is polishing away the hydroxylapetite or titanium spray layer using traditional dental abrasives on rotary drills. This approach is technically difficult because the drill rotates about an axis different from that of the implant. There is a tendency to gouge into the implant unevenly, since the point of contact is always tangent to the curve of the implant's surface. The drill will also spin out from where it is positioned, making the technique difficult. Because these things are so, lacerating the gums and bone is possible. Yet another difficulty and inadequacy of this technique is proper cooling of the implant during the procedure from friction. Heat build-up kills bone cells and will cause more of the implant to be exposed. Yet another inadequacy of this approach is that is time consuming.

OBJECTS AND SUMMARY

It is the general object of this invention to provide a device for removing and polishing implant surfaces and surface materials that are not covered by bone.

A more specific object of the invention is to provide adequate instrumentation which can be mass produced to be used on substantially all commercially used root form, cylinder and screw implants.

Another object of this invention is to provide adequate instrumentation which can be used with minimal risk to the patient concerning dentist induced injury.

Another object of this invention is to provide adequate instrumentation which is effective yet simply and quickly used.

Another object of this invention is to provide proper instrumentation that fits existing dental drills.

Another object of the invention is to allow the patient to be relatively comfortable during the procedure.

Yet another object of the invention is to provide instrumentation which can be conventionally sterilized or disposable.

Another object of this invention is to provide instrumentation which can be produced relatively inexpensively.

These and other objects of the invention are attained by a trephine-type drill with a latch-type shank having a hollow bore extending from the center of the latch to the internal aspect of the trephine through which a cannula can be inserted to cool and irrigate the field. An abrasive element is attached to the working end of the trephine by standard industrial means. The inner diameter of the working end of the trephine equals the outer diameter of industry standard implants, i.e. 4.25 millimeters, 4.0 millimeters, 3.50 millimeters, 3.30 millimeters, and 3.25 millimeters and others. The thickness of the abrasive material deposited within the abrasive element is substantially equal to the thickness of the HA or titanium coating (i.e. 20–100 microns, preferably 65 microns). Therefore, when the drill is placed over the implant such that the abrasive end covers the exposed portion of the implant, it is free to rotate about the long axis of the implant, thereby evenly and expeditiously removing and polishing the surfaces. Various abrasive elements standard to the industry can be impregnated on to the abrasive element in consecutively smaller inside diameters and smaller grits such that a serially smoother finish will be achieved. Also, various working lengths could be fabricated; or one long size cut down to size.

One specific embodiment of the invention includes a "snap on" abrasive element which can be serially changed to smaller grit size elements.

In another embodiment, linear calibrations and drain holes are included to provide depth and drainage from inside the instrument.

Yet another embodiment includes a one piece instrument made from industry standard plastic or metal which is used once and discarded. In this embodiment, the instrument's abrasive end could be shortened using a sharp instrument for a customized length.

Another embodiment includes an abrasive end which is screwed into the drill end, counter to the direction of the drill's rotation.

Inclusive on all embodiments are linear calibrations and drainage holes.

DETAILED DESCRIPTION OF THE DRAWINGS

Figure 1:
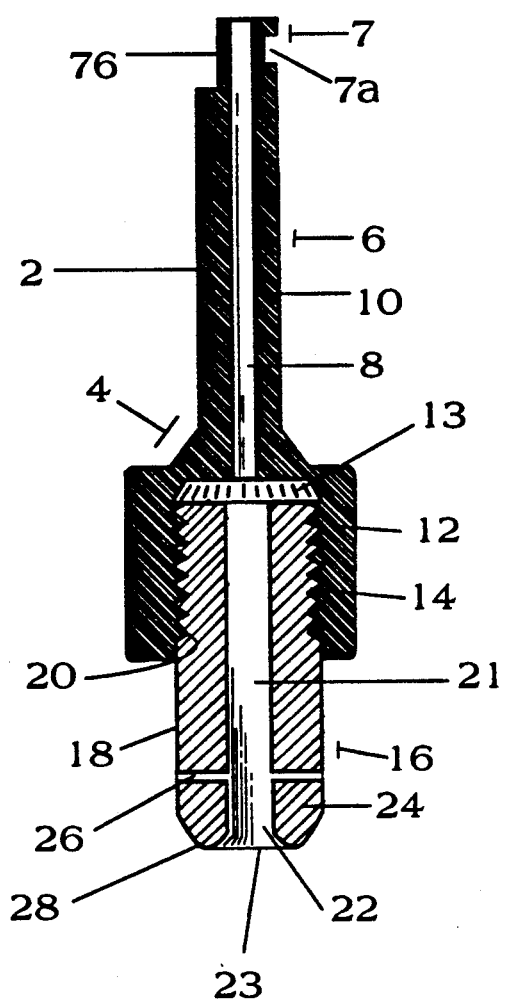
FIG. 1 is an elevation in section showing the apparatus of the present invention.

Turning now to the drawings, FIG. 1 shows the apparatus generally designated 2. The apparatus comprises a trephine-type drill 4. Drill 4 comprises a latch-type shank 6 comprising a latch 7 which includes a circumferential latch groove 7a and drive flat 7b.

Figure 3:
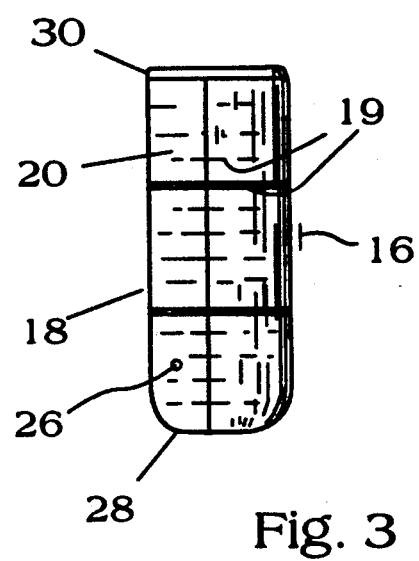
FIG. 3 is an elevation of the outside of an abrasive element such as shown in FIG. 1.

Hollow bore 8 provides fluid communication between a cannula of the drill drive, not shown, and the inside 13 of the trephine 12. The inside surface of trephine 12 comprises threads 14 for receiving abrasive element 16. Threads 14 engage the outside surface 18 of abrasive element 16 at a thread engaging portion 20. As is shown on FIG. 3, this thread engaging portion 20 may be supplied as a smooth surface which deforms to conform to threads 14 (FIG. 1) as it is screwed thereinto. As the usual "forward" rotation of a dentist drill is observed as counter-clockwise when facing the drill tip, the threads will preferably screw in clockwise, and will tend to tighten as driven.

Calibration marks 19 (FIG. 3) are provided on surface 18 at milimeter intervals to aid the dentist's judgement.

Figure 2:
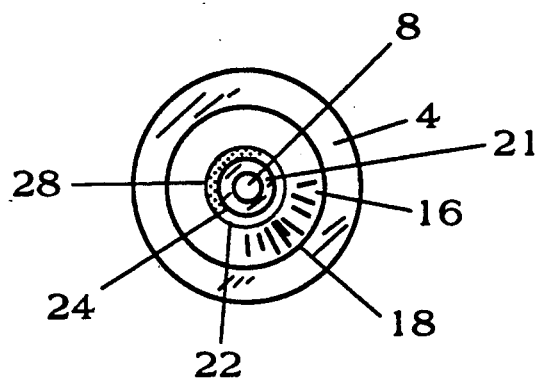
FIG. 2 is a plan view from beneath said apparatus.

As in FIGS. 1 and 2, abrasive element 16 has a hollow bore 21 therethrough. Inside surface 22 of said element defines said bore and is coated with a layer 24 of abrasive. This abrasive may be a silicone oxide, zirconium, zirconium oxide, diamond grit, or nylon filament on a matrix of silicone rubber or plastic for fixing said abrasive layer to the inside surface 22 of abrasive element 16. This matrix may be formed during the process of molding abrasive element 16. For example, the mold can be coated, on the mold wall which will mold inside surface 22, with an abrasive powder prior to the injection of the substrate material of which element 16 is mostly comprised. The coating ends at line 23 just above the lower rim of the element, to allow abrasion of the implant surface without unduly abrading the bone surface.

The substrate of abrasive element 16 preferably has the hardness of a relatively hard eraser, and may be comprised of rubber, silicone rubber, plastic or other flexible, resiliently deformable strong and firm materials which would be soft relative to the surface of the implant and of the bone or teeth. Such materials would compress elasticly against bone, tooth, or implant. Such materials would be of appropriate density to allow rapid cooling of the operative field.

As shown in FIG. 1, one or multiple drain holes 26 should be bored between outer surface 18 and inner surface 22 of abrasive element 16. Thus, when a lubricating fluid such as water is injected via a cannula through bore 8 and into bore 21, the excess is allowed to drain off through holes 26. Thus, excessive fluid pressure is prevented. Balancing the holes symmetrically to either side of bore 21 is less likely to result in a rotationally unbalanced element. FIG. 2 shows bore 8 communicating with bore 21 in plan view.

Water delivered should be of sufficient volume or coolness to maintain the implant below a temperature where bone called vitality would be adversely affected.

Figure 4:
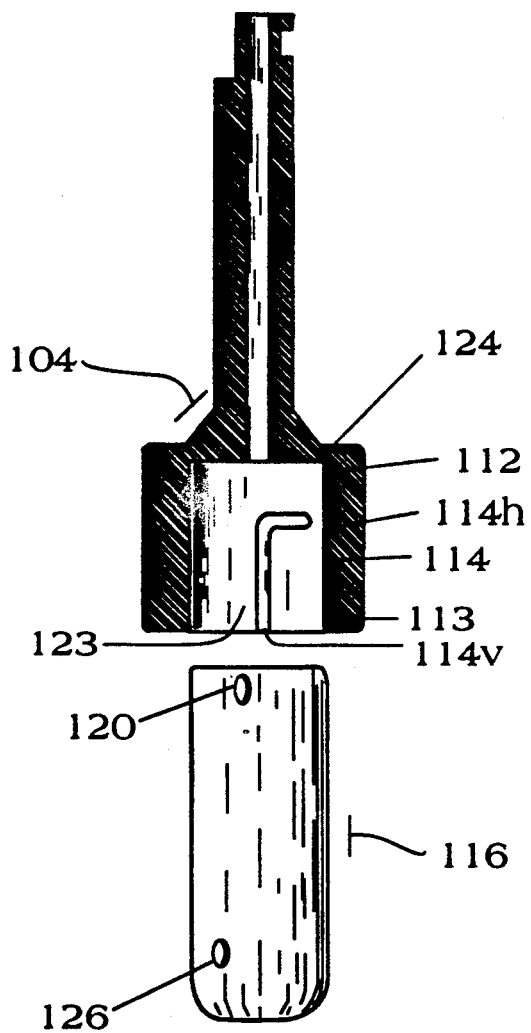
FIG. 4 is an elevation showing the separate elements of an alternative embodiment of the present invention, the trephine-type drill shown in section and the abrasive element which is insertable therein shown not in section.

FIG. 4 shows an alternative embodiment of the apparatus. A trephine-type drill 104 has a trephine 112 comprising an inner surface 113. Inner surface 113 has engraved thereon a slot 114. Slot 114 includes a vertical groove 114v and a horizontal groove 114h.

Abrasive element 116 has a locking pin 120 driven or molded diametrically therethrough with ends protruding on either side of the circumference of element 116. The size of the pin 120 and the slots 114 enable these elements to cooperate in retaining element 116 in place in trephine drill 104. The ends of pin 120 are slid into vertical slot 114v and the entire abrasive element 116 is rammed into the cavity formed by inside wall 113 of trephine 112. Element 116 is then rotated clockwise as seen when facing the drill tip, to engage horizontal slot 114h by pin 120. Abrasive element 116 is then held by friction, and by compression of its upper portion between pin 120 and the horizontal surface 124 of cavity 123.

Figure 5:
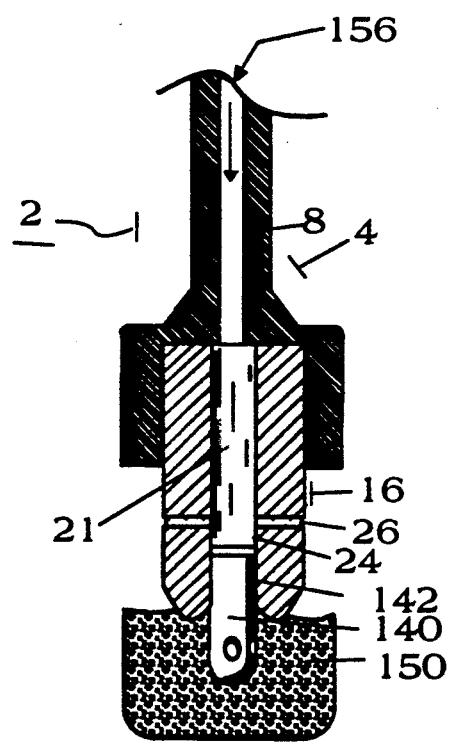
FIG. 5 is an elevation in section of the apparatus of the present invention as it is being used to polish a dental implant embedded in a jaw bone. The implant is not shown in section. The jaw bone is.

FIG. 5 shows the apparatus in operation. Implant 140 is embedded in jaw bone 150. Its outer surface 142 is engaged by inner surface 24 of abrasive element 16 which encircles implant 140. The entire apparatus 2 is rotated coaxially about the implant, so that internal surface 24 hones and polishes outer surface 142 of implant 140. To lubricate, cool, and flush debris from the operation, water 156 is injected down bore 8 through bore 21 and contacts implant 140, cooling it from inside and lubricating its outside. Excess water escapes through drain holes 26.

An O-ring 170 may be provided recessed into a circumferential undercut 172 in the inside wall 14 of the trephine. O-ring 170 seals water 156 from leaking between abrasive element 16 and inside wall 14.

Wall thickness 174 of abrasive element 16, is sufficiently thin to clear adjacent teeth or implants.

Having thus described my invention, I claim:

1. An apparatus for repairing a dental implant having a cylindrical core and an external cylindrical surface, said apparatus comprising:

shank means for mounting upon a dental drill drive, said shank means having shank bore means for delivering fluid to a hollow circular bore in an abrasive element for lubricating and cooling the dental implant during abrasive polishing operations;

mounting means affixed to said shank means for mounting the abrasive element; and the abrasive element, said abrasive element comprising the hollow circular bore defined by a bore wall, and a substantially radial bore extending through said abrasive element for draining said lubricating and cooling fluid, said bore wall comprising an outer internal diameter adapted for closely fitting said external cylindrical surface of said dental implant, a plurality of abrasive units affixed upon said outer internal diameter and projecting radially inward such as to define an inner internal diameter equal to said outer internal diameter minus the average radially inward projection of said abrasive units, said inner internal diameter being substantially equal to the diameter of said cylindrical core of said dental implant, said abrasive units being of a hardness greater than said external cylindrical surface of said dental implant.

2. Apparatus according to claim 1 further comprising: latch means for engagement with a standard dental drill drive.

3. The invention of claim 1 wherein said abrasive element further comprises calibration marks on an external surface of said abrasive element.

4. The invention of claim 3 wherein said calibration marks are perpendicular to an axis of rotation of said abrasive element and spaced at one millimeter intervals, and said marks comprise means for guiding accurate trimming of the abrasive element across its cylindrical altitude to facilitate clearance polishing implants of various vertical dimensions and comprise means for aiding a dentist's judgment during a polishing operation.

5. The invention of claim 1 wherein said abrasive units are of a material selected from the group consisting of silicon oxide, pumice, zirconium, zirconium oxide, diamond, and nylon filaments.

6. The invention of claims 1 wherein said outer internal diameter is in the range of 3.25 millimeters through 4.25 millimeters.

7. The invention of claim 1 wherein said outer internal diameter is selected from a group consisting of the following substantial dimensions:
4.25 mm,
4.0 mm,
3.3 mm
3.5 mm, and
3.25 mm.

8. An abrasive element for polishing a dental implant having a cylindrical core and an external surface, said abrasive element comprising:
a cylindrical structure;
said structure having means for engaging a dental drill attachment means for driving said abrasive element in a rotary motion around a central axis;
said structure comprising a resiliently compressible substrate of a hardness substantially less than an osseous surface and than a dental implant surface;
said element having an internal cylindrical bore through said substrate, said bore defined by an internal wall;
said internal wall comprising:
an outer internal diameter adapted to closely fitting said external cylindrical surface of said dental implant;
a plurality of abrasive units affixed upon said outer internal diameter and projecting radially inward such as to define an inner internal diameter equal to said outer internal diameter minus the average radially inward projection of said abrasive units;
wherein said inner internal diameter is substantially equal to the diameter of said cylindrical core of said dental implant; and
wherein said abrasive units are of a hardness greater than said external cylindrical surface of said dental implant.

9. The invention of claim 8 wherein said abrasive element further comprises calibration marks on an external surface of said abrasive element.

10. The invention of claim 8 wherein said calibration marks are perpendicular to an axis of rotation of said abrasive element and spaced at one millimeter intervals, and said marks comprise means for guiding accurate trimming of the abrasive element across its cylindrical altitude to facilitate clearance polishing implants of various vertical dimensions and comprise means for aiding a dentist's judgment during a polishing operation.

11. The invention of claim 8 wherein said abrasive units are of a material selected from the group consisting of silicon oxide, pumice, zirconium, zirconium oxide, diamond, and nylon filaments.

12. The invention of claims 8 wherein said outer internal diameter is in the range of 3.25 millimeters through 4.25 millimeters.

13. The invention of claim 8 wherein said outer internal diameter is selected from a group consisting of the following substantial dimensions:
4.25 mm,
4.0 mm,
3.3 mm
3.5 mm, and
3.25 mm.

14. A method of polishing an outer cylindrical surface of a dental implant, said method comprising the steps of:
locating an abrasive element, having a hollow internal bore defined by an inner abrasive surface, with its bore substantially concentric over said implant, said implant located within a mouth;
engaging the inner abrasive surface of the abrasive element with the outer surface of the implant;
rotating the abrasive element; and
polishing said implant with rotary motion of the abrasive surface around said implant.

15. A method according to claim 14 in which a lubricating, cooling, and flushing fluid such as water is delivered to the internal bore of the abrasive element to lubricate and cool the implant during the polishing operation.

16. A method according to claim 15 in which the steps are serially repeated using abrasive elements having successively finer abrasive grits.

* * * * *